(12) United States Patent
Fitzpatrick et al.

(10) Patent No.: US 6,955,806 B2
(45) Date of Patent: Oct. 18, 2005

(54) IONENE POLYMERS AND THEIR USE AS ANTIMICROBIAL AGENTS

(75) Inventors: Richard J. Fitzpatrick, Marblehead, MA (US); Keith K. Shackett, Athol, MA (US); Jeffrey D. Klinger, Sudbury, MA (US)

(73) Assignee: Genzyme Corporation, Cambridge, MA (US)

( * ) Notice: Subject to any disclaimer, the term of this patent is extended or adjusted under 35 U.S.C. 154(b) by 9 days.

(21) Appl. No.: 10/051,765

(22) Filed: Jan. 17, 2002

(65) Prior Publication Data

US 2003/0031644 A1 Feb. 13, 2003

Related U.S. Application Data

(60) Provisional application No. 60/262,586, filed on Jan. 18, 2001.

(51) Int. Cl.[7] ................... A61K 31/785; A61K 31/74; A61F 13/00; C08G 73/06
(52) U.S. Cl. ................ 424/78.36; 424/78.1; 424/402; 424/70.12; 424/422; 528/423
(58) Field of Search ............................ 424/78.36, 78.1, 424/402, 70.12, 422, 78.08; 528/423

(56) References Cited

U.S. PATENT DOCUMENTS

| | | |
|---|---|---|
| 3,641,034 A | 2/1972 | Simon |
| 3,652,149 A | 3/1972 | Rogers |
| 3,770,476 A | 11/1973 | McKay |
| 3,874,870 A | 4/1975 | Green et al. |
| 3,923,973 A | 12/1975 | Green et al. |
| 3,929,990 A | 12/1975 | Green et al. |
| 3,931,319 A | 1/1976 | Green et al. |
| 3,946,035 A | 3/1976 | Jacquet et al. |
| 3,961,042 A | 6/1976 | Green et al. |
| 3,966,906 A | 6/1976 | Schultze et al. |
| 3,988,158 A | * 10/1976 | Muramatsu et al. ........ 430/635 |
| 4,025,617 A | 5/1977 | Green et al. |
| 4,025,627 A | 5/1977 | Green et al. |
| 4,025,653 A | 5/1977 | Green et al. |
| 4,027,020 A | 5/1977 | Green et al. |
| 4,113,709 A | 9/1978 | Quinlan |
| 4,157,387 A | 6/1979 | Benedict |
| 4,206,295 A | 6/1980 | Wagner et al. |
| 4,217,429 A | 8/1980 | Wagner et al. |
| 4,379,137 A | 4/1983 | Ehlers et al. |
| 4,506,081 A | 3/1985 | Fenyes et al. |
| 4,778,813 A | 10/1988 | Fenyes et al. |

(Continued)

FOREIGN PATENT DOCUMENTS

| | | |
|---|---|---|
| CA | 2048233 | 5/1992 |
| EP | 0366853 A1 | 5/1990 |
| EP | 0411 111 B1 | 8/1990 |
| EP | 0392492 A2 | 10/1990 |
| GB | 1 546 809 | 5/1979 |
| JP | 59-217787 | 12/1984 |
| JP | 60-229025 | 11/1985 |
| JP | 60-229027 | 11/1985 |
| JP | 62-51138 | 3/1987 |
| JP | 62-62881 | 3/1987 |
| JP | 2000280622 | 10/2000 |
| SU | 476257 | 5/1976 |
| WO | WO 90/09405 | 8/1990 |
| WO | WO 94/14872 | 7/1994 |
| WO | WO 96/20737 | 7/1996 |
| WO | WO 98/02136 | 1/1998 |
| WO | WO 99/02621 | 1/1999 |
| WO | WO 99/55320 | 11/1999 |

OTHER PUBLICATIONS

Jegal, et al., "Development of Polyion Complex Membranes for the Separation of Water–Alcohol Mixtures.I. Synthesis and Physical Properties of the Polycations Based on 1,3–Di (4–pyridyl) propane", J. Appl. Polymer Science, 54: 65–72 (1994).

Jegal, et al., "Development of Polyion Complex Membranes for the Separation of Water–Alcohol Mixtures. III. Preparation of Polyion Complex Membranes Based on the k–Carrageenan for the Pervaporation Separation of Water–Ethanol", J. Appl. Polymer Sci., 60:1177–1183 (1996).

Kanazawa, et al., "Polymeric Phosphonium Salts as a Novel Class of Cationic Biocides. IV. Synthesis and Antibacterial Activity of Polymers with Phosphonium Salts in the Main Chain", J. Polymer Sci.; Part A: Polymer Chemistry 31:3031–3038 (1993).

Nohira, et al., "Synthesis of Poly(alkylenediphenylphosphonium bromide", Kobunshi Ronbunshu, 31(6):391–394 (1974).

Rembaum, et al., "Interaction of Living Cells with Polyionenes and Polyionene–Coated Surfaces", J.Biomed. Mater. Res. Symposium 8: 101–110 (1977).

Yi, et al., "The Synthesis and Reduction Behavior of Substituted Polypropylviologens", Acta Scientiarum Naturalium Universitatis Sunyatseni No. 2: 30–36(1986).

(Continued)

Primary Examiner—Thurman K. Page
Assistant Examiner—Blessing Fubara
(74) Attorney, Agent, or Firm—Hamilton, Brook, Smith & Reynolds, P.C.

(57) ABSTRACT

Disclosed are ionene polymers having antimicrobial activity. "Ionene polymers" as used in this invention are cationic polymers in which a substantial proportion of the atoms providing the positive charge are quaternized nitrogens located in the main polymeric chain or backbone of the polymer rather than in pendant groups. Also disclosed are antimicrobial compositions comprising ionene polymers and methods for treating microbial infections in mammals comprising the step of administering to a mammal, a therapeutically effective amount of at least one antimicrobial composition of the invention. Also disclosed are antimicrobial compositions comprising at least one ionene polymer and methods for preventing, inhibiting or eliminating the growth, dissemination, and/or the accumulation of microorganisms on a susceptible surface (including, but not limited to, the formation of biofilms on a susceptible surface) comprising the step of contacting such surface with a composition of the invention.

26 Claims, No Drawings

U.S. PATENT DOCUMENTS

| | | | |
|---|---|---|---|
| 4,898,808 A * | 2/1990 | Tachibana et al. | 430/510 |
| 4,923,619 A | 5/1990 | Legros | |
| 4,960,590 A | 10/1990 | Hollis et al. | |
| 4,980,067 A | 12/1990 | Hou et al. | |
| 5,128,100 A | 7/1992 | Hollis et al. | |
| 5,142,002 A | 8/1992 | Metzner | |
| 5,149,524 A | 9/1992 | Sherba et al. | |
| 5,256,420 A | 10/1993 | Tsao et al. | |
| 5,283,316 A * | 2/1994 | Dominguez et al. | 528/397 |
| 5,300,287 A | 4/1994 | Park | |
| 5,352,833 A | 10/1994 | Merianos | |
| 5,419,897 A * | 5/1995 | Drake et al. | 424/78.1 |
| 5,451,398 A | 9/1995 | Vigh | |
| 5,575,917 A | 11/1996 | Konstantin et al. | |
| 5,575,993 A | 11/1996 | Ward et al. | |
| 5,616,317 A | 4/1997 | Nagase et al. | |
| 5,637,308 A | 6/1997 | Del Corral et al. | |
| 5,646,205 A | 7/1997 | Lee et al. | |
| 5,668,084 A | 9/1997 | Unhoch et al. | |
| 5,681,862 A | 10/1997 | Hollis et al. | |
| 5,709,976 A | 1/1998 | Malhotra | |
| 5,843,865 A | 12/1998 | Del Corral et al. | |
| 5,866,016 A | 2/1999 | Jaquess et al. | |
| 6,007,803 A | 12/1999 | Mandeville, III et al. | |
| 6,016,508 A | 1/2000 | Chu et al. | |
| 6,034,129 A | 3/2000 | Mandeville, III et al. | |
| 6,123,928 A | 9/2000 | Sovak et al. | |
| 2001/0041485 A1 | 11/2001 | Zhao et al. | |
| 2003/0021761 A1 * | 1/2003 | Fitzpatrick et al. | 424/78.1 |

OTHER PUBLICATIONS

Brown, A.E., "Overview of fungal infections in cancer patients," *Seminars in Oncology*, 17(3) SUPPL 6:2–5 (1990) (Abstract).

Epstein, J.B., et al., "Prophylaxis of candidiasis in patients with leukemia and bone marrow transplants," *Oral Surg. Oral Med. Oral Path. Oral Radiol. and Endodontics*, 81(3):291–296 (1996).

Gibson, J., et al., "Oral staphylococcal mucositis: A new clinical entity in orofacial granulomatosis and Crohn's disease," *Oral Surg. Oral Med. Oral Path. Oral Radiol. and Endodontics*, 89(2):171–176 (2000).

Mosca, D.A., et al., "IB–367, a protegrin peptide with in vitro and in vivo activites against the microflora associated with oral mucositis," *Antimicrobial Agents and Chemotherapy*, 44(7):1803–1808 (2000).

Ferretti, G.A., et al., "Therapeutic use of chlorhexidine in bone marrow transplant patients: case studies," *Oral Surg. Oral Med., and Oral Pathol.*, 63(6):683–687 (1987).

Mulholland, B., et al., "The antimicrobial activity of protamine and polybrene," *J. Hosp. Infection*, 10:305–307 (1987).

Kourai, H., et al., "The Antimicrobial Characteristics of Poly [dimethyliminio (polymethylene) chloride]s," *J. Antibact. Antifung. Agents*, 22(9):519–530 (1994).

Database CA [Online] Chemical Abstracts Service, Columbus, OH. Nagase, Hiroshi et al., "Synergistic microbicide compositions and control of microorganisms with them," (retrieved from STN). Accession No. 130:263534.

Database CA [Online] Chemical Abstracts Service, Columbus, OH. Nagase, Hiroshi et al., "Synergistic compositions and method for control of microorganisms in water systems using ionene polymers and metal ions," (retrieved from STN). Accession No. 130–233638.

Database CA [Online] Chemical Abstracts Service, Columbus, OH. Koma, Hiroki et al., "Sterilization of the hands with solutions containing microbicidal vinyl copolymers," (retrieved from STN). Accession No. 122:99309.

Database CA [Online] Chemical Abstracts Service, Columbus, OH. Koma, Hiroki et al., "Biofouling inhibitors for industrial aqueous systems" (retrieved from STN). Accession No. 113:120571.

* cited by examiner

IONENE POLYMERS AND THEIR USE AS ANTIMICROBIAL AGENTS

RELATED APPLICATION

This application claims the benefit of U.S. Provisional Application No. 60/262,586, filed on Jan. 18, 2001. The entire teachings of the above application are incorporated herein by reference.

BACKGROUND OF THE INVENTION

Infectious microorganisms such as bacteria, fungi, algae, viruses, mildew, protozoa, and the like are capable of growing on a wide variety of living and non-living surfaces, including skin, teeth, mucosa, vascular tissue, medical implants, and medical devices. Invasive microbial infections of living organisms (e.g. bacterial, viral, protozoal, parasitic, fungal, etc.) can effect various organs of the body. Such infections are generally treated with well-characterized antimicrobial agents that may be safely tolerated by the host organism. However, the resistance of microorganisms to various antimicrobial agents has increased at an alarming rate rendering many important therapeutics for the treatment of microbial infections ineffective. Microorganisms employ one or more modes of resistance, often rendering them polyresistant. In particular, a great need still exists for effective antimicrobials for wound management and infections of the skin, oral mucosa and gastrointestinal tract. Individual microorganisms not attached to or growing on a surface are referred to as "planktonic".

These planktonic organisms are responsible for invasive and disseminated infections in the host, when it is a living organism. Such planktonic organisms are the targets of conventional antimicrobial therapy.

When planktonic microorganisms grow and disseminate on non-living surfaces, they may cause contamination and biofouling of that surface. In many cases a microorganism can grow and accumulate on a surface to the point of becoming almost impossible to remove. This accumulation takes place through the formation of biofilms. A biofilm occurs when one or more microorganisms attach to a surface and secrete a hydrated polymeric matrix that surrounds them. Microorganisms existing in a biofilm, termed sessile, grow in a protected environment that insulates them from attack from antimicrobial agents. These sessile communities can give rise to nonsessile planktonic organisms, which rapidly multiply and disperse over the surface. Once again, it is these planktonic organisms that are the targets of conventional antimicrobial treatments such as antibacterial and antifungal agents. However, these conventional treatments fail to eradicate the sessile communities rooted in the biofilm. Biofilms are understood to be a frequently occurring reservoir for infectious agents and pose tremendous problems for the health-care industry. The biology of biofilms is described in more detail in *Bacterial biofilms: a common cause of persistent infection*" J. Costerson, P. Steward, E. Greenberg, *Science* 284: 1318–1322 (1999).

Microbial contamination and biofilms adversely affect the health care industry and other industries wherein microbial contamination poses a health risk to humans such as public water supplies, and food production facilities. Infections involving implanted medical devices, for example, generally involve biofilms, where a sessile community provides a reservoir for an invasive infection. Antibodies and host immune defenses are ineffective in killing the organisms contained in a biofilm even though these organisms have elicited the antibody and related immune response. Antibiotics typically treat the infection caused by the planktonic organisms, but fail to kill those sessile organisms protected in the biofilm. Therefore, even if the contaminated medical device were removed from the host, any replacement device will be particularly susceptible to contamination from the residual microorganisms in the area from which the medical device was removed.

Since the difficulties associated with eliminating biofilm-based infections and contamination are well-recognized, a number of technologies have developed to prevent or impair biofilm formation. These technologies include the development of various biocidal agents that are brought in contact with the contaminated or susceptible surface. However, any agent used to impair biofilm formation must be safe for use by humans and other non-target organisms. Biocides known to be effective at eliminating growth of unwanted microorganisms are generally toxic or otherwise harmful to humans, animals or other non-target organisms. Biocides known to be safe to non-target organisms, are generally less effective at preventing or eliminating microorganism growth, and require frequent application to the target surface.

Thus there is a need for antimicrobials that are safe, non-toxic, long-lasting and effective at controlling contamination and infection by unwanted microbial organisms, with minimal development of resistant or polyresistant microorganisms.

SUMMARY OF THE INVENTION

In one aspect, the present invention relates to novel, antimicrobial polymers.

In another aspect, the present invention relates to antimicrobial pharmaceutical compositions and methods for treatment of microbial infections in a mammal.

In another aspect, the present invention relates to antimicrobial pharmaceutical compositions and methods for wound management.

In another aspect, the present invention relates to antimicrobial pharmaceutical compositions and methods for treatment of infections of the skin, oral mucosa and gastrointestinal tract.

In yet another aspect, the present invention relates to antimicrobial compositions and methods of preventing, inhibiting, or eliminating the growth, dissemination and accumulation of microorganisms on susceptible surfaces, particularly in a health-related environment.

In accordance with these and other aspects, the present invention provides novel ionene polymers having antimicrobial activity. "Ionene polymers" or "polyionenes," as used in the present invention, are cationic polymers or copolymers with quaternized nitrogen or phosphorus located in the main polymeric chain or backbone of the polymer, providing a positive charge. Polyionenes can also be polyguanidines or copolymers thereof, where the cationic nitrogen atom is an imide nitrogen directly bonded to the polymer backbone. The ionene polymers of this invention have been found to be non-irritating and low in toxicity to warm-blooded animals. The present invention also provides antimicrobial compositions comprising ionene polymers and methods for treating microbial infections in mammals comprising the step of administering to a mammal, a therapeutically effective amount of at least one antimicrobial composition of the invention. The present invention further provides antimicrobial compositions comprising at least one ionene polymer and methods for preventing, inhibiting or eliminating the growth, dissemination, and/or the accumulation of microorganisms on a susceptible surface (including, but not limited to, the formation of biofilms on a susceptible surface) comprising the step of contacting such surface with a composition of the invention.

Additional advantages of the invention will be set forth in part in the description which follows. It is to be understood that both the foregoing general description and the following general description are exemplary and explanatory only and are not restrictive of the present invention as claimed.

DETAILED DESCRIPTION OF THE INVENTION

It is known that quaternary ammonium compounds have antimicrobial characteristics, particularly with regard to the prevention or elimination of microbial contamination of aqueous systems also known as biofouling. However, few, if any of such compounds have been found to have all the necessary characteristics (e.g., low toxicity, high potency or efficacy, long acting) for use as human pharmaceuticals or in a health-related environment wherein activities are carried out that are directly or indirectly implicated in the restoration or maintenance of human health.

The present invention relates to ionene polymers that are particularly suitable for use in pharmaceutical compositions for treatment of microbial infections in mammals as well as for use in the prevention, inhibition or elimination of the growth, dissemination, and/or the accumulation of microorganisms on a susceptible surface (including, but not limited to, the formation of biofilms). Particular susceptible surfaces include those surfaces that are in intimate contact with humans such as medical devices, medical implants, wound dressings and the like.

Ionene polymers may be classified according to the repeating unit found in the polymer. The repeating unit results from the reactants used to make the ionene polymer. Methods of preparing preferred polymers of the invention are included in the Examples.

One embodiment of the present invention is a "piperidinium" ionene polymer or copolymer comprising the repeating unit of formula I:

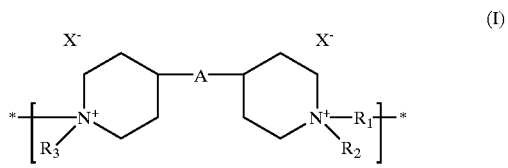

(I)

$R_1$ is a substituted or unsubstituted lower alkylene group;

$R_2$ and $R_3$ are each independently hydrogen or a substituted or unsubstituted lower alkyl group.

A is a bond or a substituted or unsubstituted lower alkylene group.

Each $X^-$, separately or taken together, is a physiologically acceptable anion.

Preferably in the repeat unit of formula I, A and $R_1$ are independently an unsubstituted straight chained lower alkylene group or a straight chained lower alkylene group substituted with —OH (e.g., one, two, or more) and $R_2$ and $R_3$ are both hydrogen, an unsubstituted straight chained lower alkylene group or a straight chained lower alkyl groups substituted with —OH, provided that at least one of A, $R_1$, $R_2$ and $R_3$ are substituted with —OH.

More preferably in the repeat unit of formula I, A is an unsubstituted straight chained lower alkylene group, $R_1$ is a straight chained lower alkylene group substituted with —OH (e.g., one, two, or more) and $R_2$ and $R_3$ are hydrogen or an unsubstituted straight chained lower alkyl group; or A and $R_1$ are unsubstituted straight chained lower alkylene groups and $R_2$ and $R_3$ are straight chained lower alkyl groups substituted with —OH.

Preferred repeat units of formula I are represented by the following group of repeat unit formulas:

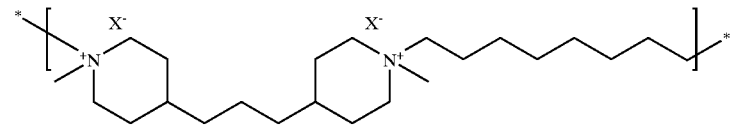

(II)

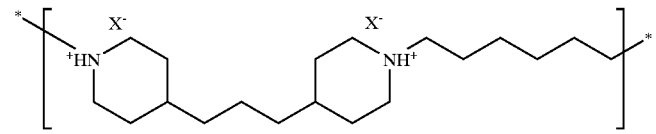

(III)

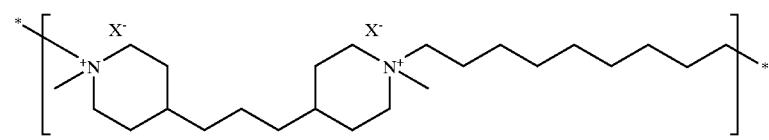

(IV)

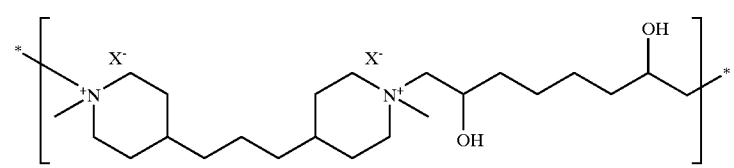

(V)

-continued

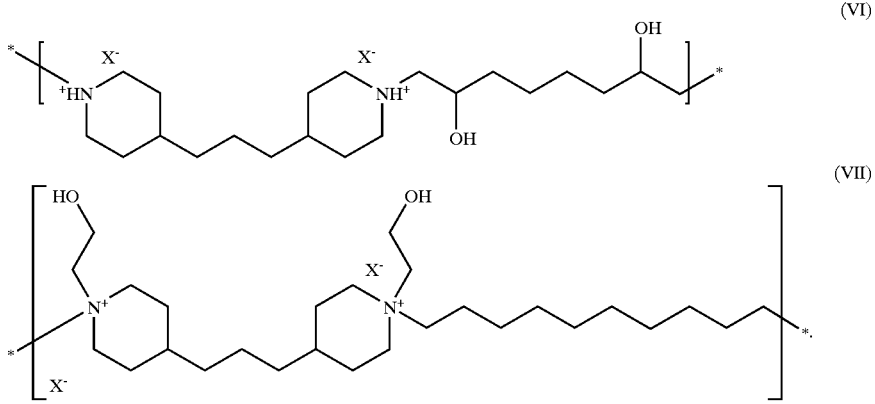

A second embodiment of the present invention is a second ionene polymer or copolymer comprising the repeat unit of formula VIIIa and the repeat unit of formula VIIIb:

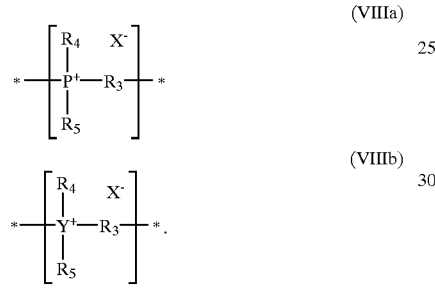

Y is P or N.

$R_3$ is a substituted or unsubstituted arylene or lower alkylene group and $R_4$ and $R_5$ are independently a substituted or unsubstituted aliphatic or aromatic group. $R_3$, $R_4$ and $R_5$ in formula VIIIa can be the same or different from $R_3$, $R_4$ and $R_5$ in formula VIIIb, but are preferably the same. Preferably, $R_3$ is a substituted or unsubstituted phenylene or lower alkylene group and $R_4$ and $R_5$ are independently a substituted or unsubstituted lower alkyl or phenyl group. More preferably, $R_3$ is an unsubstituted phenylene or lower alkylene group and $R_4$ and $R_5$ are independently an unsubstituted lower alkyl or phenyl group.

Each $X^-$ in the polymer or copolymer, separately or taken together, is a physiologically acceptable anion.

The second ionene polymer can be a homopolymer when the repeat unit of formula VIIIa is the same as the repeat unit of formula VIIIb, i.e., when Y is P.

In a preferred embodiment, the second ionene polymer or co-polymer comprises repeating units of formula IX:

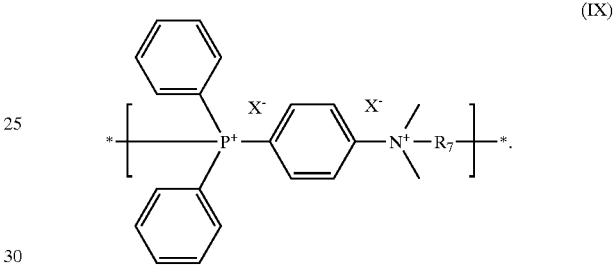

$R_7$ is a substituted or unsubstituted lower alkylene group having from 1 to about 24 carbon atoms, preferably from about 4 to about 12 carbon atoms.

Each $X^-$, separately or taken together, is a physiologically acceptable anion.

Specific examples of the second ionene polymer or copolymer comprise repeat units of formulas X and XI.

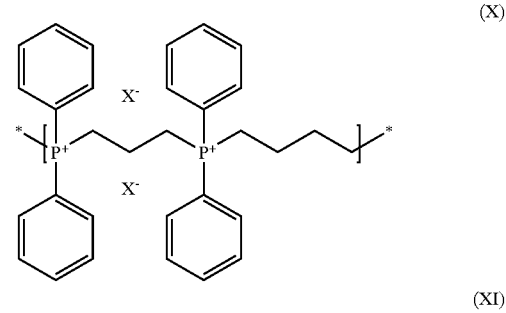

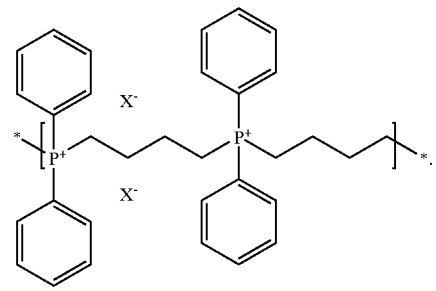

A third embodiment of the present invention is a "guanidine" ionene polymer or copolymer comprising the repeating unit of formula XII:

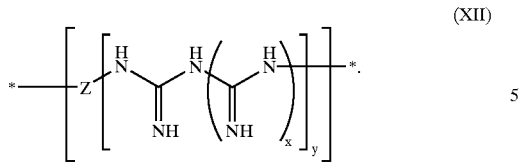
(XII)

Z is a substituted or unsubstituted lower alkylene or lower alkylene glycol group, preferably an unsubstituted lower alkylene or lower alkylene glycol group; x is an integer from 1–4; and y is an integer from 2–5. In a preferred embodiment, Z is an unsubstituted lower alkylene or lower alkylene glycol group and x is 1 and y is 2; x is 1 and y is 3; x is 1 and y is 4; or x is 1 and y is 5. Specific examples of guanidine ionene polymers and copolymers comprise repeat units of formulas XIII and XIV.

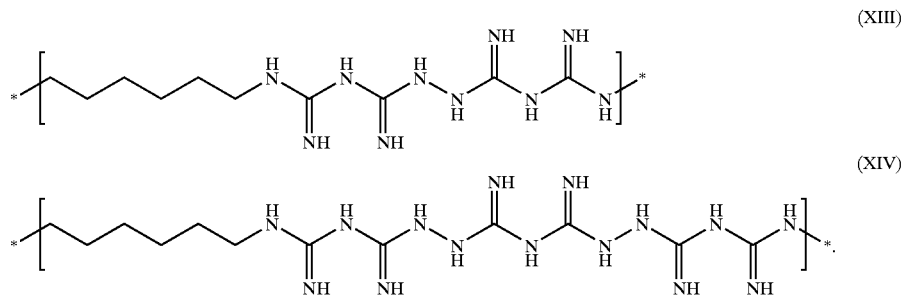
(XIII)

(XIV)

Other guanidine copolymers include copolymers comprising a repeat unit of formula XII alternating with a repeat unit of formula I–XI, XV, XVI, XIX, XX, XXII, or XXIII.

Another embodiment of the present invention is a "pyridinium" ionene polymer or copolymer comprising repeating units of formula XV:

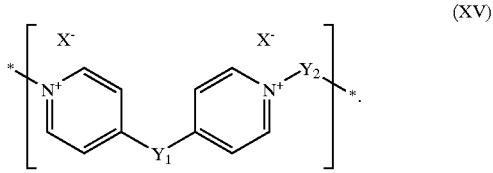
(XV)

$Y_1$ and $Y_2$ are independently a lower alkylene or lower alkylene glycol group. Preferably, at least one of the lower alkylene or lower alkylene glycol groups represented by $Y_1$ and $Y_2$ is substituted. More preferably, the lower alkylene or lower alkylene glycol groups represented by $Y_1$ and $Y_2$ are straight chained. Even more preferably, the lower alkylene or lower alkylene glycol groups represented by $Y_1$ and $Y_2$ are straight chained and at least one (preferably $Y_2$) is substituted with one, two or more alcohol groups (e.g., $Y_2$ is —$CH_2CHOH(CH_2)_nCHOHCH_2$, where n is an integer from 0 to 8). Each $X^-$, separately or taken together, is a physiologically acceptable anion. Preferably, pyridinium ionene polymers and copolymers are substantially free of diphenols. "Substantially free" means that pyrdinium ionene polymers and copolymers comprise less than 5% diphenol, preferably less than 2% diphenol, even more preferably less than 1% diphenol, or ideally no diphenol (i.e., a homopolymer).

Specific examples of pyridinium ionene polymers and copolymers comprise repeat unit of formulas XVI and XVII:

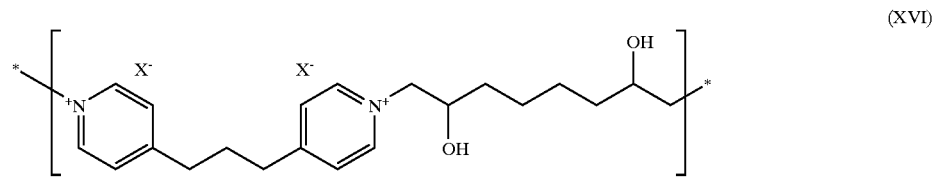
(XVI)

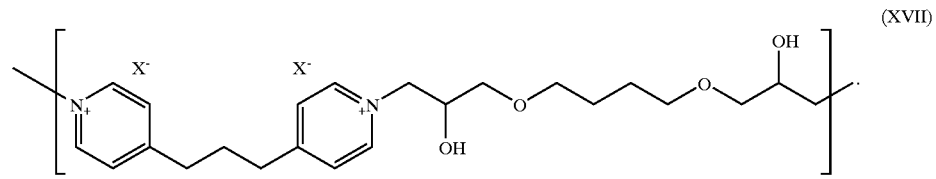
(XVII)

Other preferred ionene polymers of the invention are represented by the following group of repeat unit formulas:

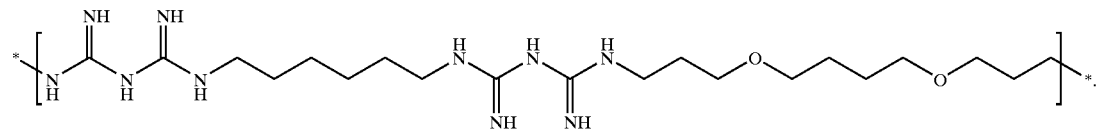
(XVIII)

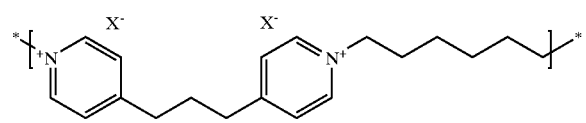
(XIX)

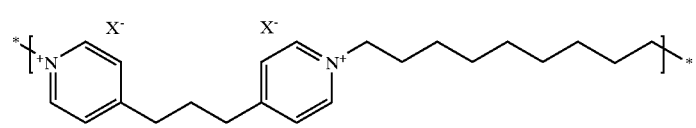
(XX)

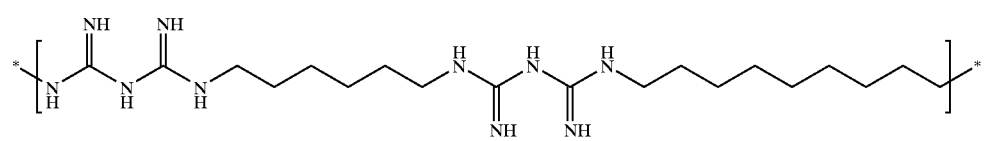
(XXI)

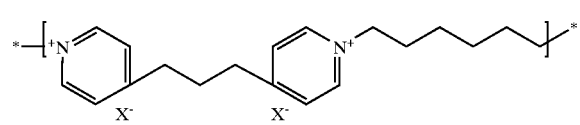
(XXII)

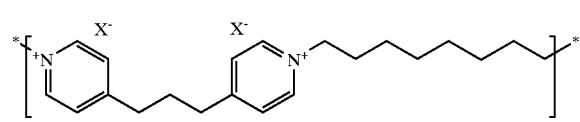
(XXIII)

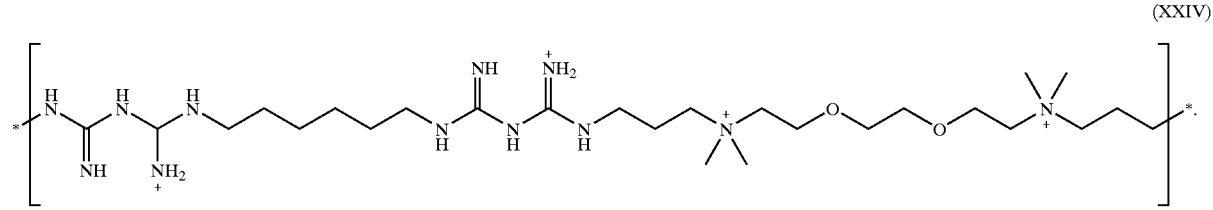
(XXIV)

It is to be understood that the variables in each repeat unit of the copolymers of the present invention are independently selected. For example, in a copolymer having repeat units of formula I, the alkylene group represented by A in one repeat unit can differ from the alkylene group represented by A in other repeat units. Preferably, however, a variable in one repeat unit represents the same group as in all other repeat units in the polymer.

An "aliphatic group" is non-aromatic, consists solely of carbon and hydrogen and may optionally contain or more units of unsaturation, e.g., double and/or triple bonds. An aliphatic group may be straight chained or branched and typically contains between about 1 and about 24 carbon atoms, more typically between about 4 and about 12 carbon atoms.

Aliphatic groups are preferably lower alkyl groups or lower alklyene groups, which include C1–24 (preferably C4–C12) straight chained or branched saturated hydrocarbons. A lower alkyl group is a saturated hydrocarbon in a molecule that is bonded to one other group in the molecule through a single covalent bond from one of its carbon atoms. Examples include methyl, ethyl, n-propyl, iso-propyl, n-butyl, sec-butyl and tert-butyl. An alkylene groups is a saturated hydrocarbon in a molecule that is bonded to two other groups in the molecule through a single covalent from two of its carbon atoms. Examples include methylene, ethylene, propylene, iso-propylene (—CH(CH$_3$)CH$_2$—), butylene, sec-butylene (—CH(CH$_3$)CH$_2$CH$_2$—), and tert-butylene (—C(CH$_3$)$_2$CH$_2$—).

A lower alkylene glycol group (or lower alkyl glycol group) is a lower alkylene group (or lower alkyl) in which one, two or more methylene groups is replaced with an oxygen atom(s) (—O—).

Aromatic groups include carbocyclic aromatic groups such as phenyl, 1-naphthyl, 2-naphthyl, 1-anthracyl and 2-anthacyl, and heterocyclic aromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidy, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl and 5-oxazolyl.

Aromatic groups also include fused polycyclic aromatic ring systems in which a carbocyclic aromatic ring or heteroaryl ring is fused to one or more other heteroaryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Phenyl is a preferred aromatic group.

"Arylene" is an aromatic ring(s) moiety in a molecule that is bonded to two other groups in the molecule through a single covalent from two of its ring atoms. Examples include phenylene [—($C_6H_4$)—], thienylene [—($C_4H_2S$)—] and furanylene [—($C_4H_2O$)—].

Suitable substituents on an aliphatic, aromatic or benzyl group are those which do not substantially decrease the antimicrobial properties of the molecule (e.g., increase the $LD_{50}$ by more than a factor of ten). Examples of suitable substituents on an aliphatic, aromatic or benzyl group include, for example, halogen (—Br, —Cl, —I and —F) —OR, —CN, —$NO_2$, —$NR_2$, —COOR, —$CONR_2$, —$SO_kR$ (k is 0, 1 or 2) and —NH—C(=NH)—$NH_2$. Each R is independently —H, an aliphatic group, a substituted aliphatic group, a benzyl group, a substituted benzyl group, an aromatic group or a substituted aromatic group, and preferably —H, a lower alkyl group, a benzylic group or a phenyl group. A substituted benzylic group or aromatic group can also have an aliphatic or substituted aliphatic group as a substituent. A substituted aliphatic group can also have a benzyl, substituted benzyl, aromatic or substituted aromatic group as a substituent. A substituted aliphatic, substituted aromatic or substituted benzyl group can have more than one substituent. A preferred substituent on an aliphatic group is —OH.

The polymers having a repeat unit represented by Formulas I–XI, XV–XVII, XIX–XX and XXII–XXIII additionally comprise physiologically acceptable anions represented by $X^-$. The anions in the polymer can be the same or different. Each $X^-$ in a repeat unit can separately be a monovalent anion, i.e., an anion having a negative charge of one. Alternatively, two or more $X^-$s in the same repeat unit or in different repeat units, taken together, can represent an anion having a negative charge of two, three or more. A polymer can comprise anions of different charges. Examples of suitable counteranions include sulfate, bisulfate, sulfite, bisulfite, phosphate, monohydrogenphosphate, dihydrogenphosphate, metaphosphate, pyrophosphate, chloride, bromide, iodide, acetate, proprionate, decanoate, caprylate, acrylate, formate, isobutyrate, caproate, heptanoate, propiolate, oxalate, malonate, succinate, fumarate, maleate, benzoate, sulfonate, phenylacetate, citrate, lactate, glycolate, tartrate and the like. Bromide and chloride are preferred. One anion can be exchanged for another by passing a solution containing the desired counter anion over the polymer.

Also included in the present invention are physiologically acceptable salts of the polymers having repeat units represented by Formulas XII–XIV, XVIII, XXI, and XXIV. Salts can be formed by reacting the polymer with a suitable acid. Examples include the corresponding acid of the salts listed in the previous paragraph. The hydrochloride and hydrobromide salts are preferred. Polymers represented by Formulas XII–XIV, XVIII, XXI, and XXIV can have up to one molecule of hydrochloride or hydrobromide for every —NHC(=NH)NH— group in the repeat unit.

As shown in the following examples, ionene polymers of the invention have been found to be effective in treating microbial infections in a mammal, and have been found to be particularly useful in treating infections of the skin, oral mucosa and gastrointestinal tract.

Ionene polymers of the invention and pharmaceutical compositions thereof provide numerous advantages over conventional therapies for treatment of microbial infections. As used herein, "conventional antimicrobial" therapies include but are not limited to well known antibacterial agents, such as vancomycin, metronidazole, penicillin, oxacillin, as well as antifungals, antiseptics and the like. Ionene polymers of the invention provide a broader spectrum of treatment than presently available antibiotics. Ionene polymers are not likely to elicit antibiotic resistance or polyresistance. Ionene polymers of the invention are not substantially degraded in the digestive tract and therefore, can be administered orally or topically. When desirable, ionene polymers of the invention may be designed such that they are not likely to be systemically absorbed by the body thus providing an attractive drug safety profile.

Therapeutically effective amounts of an ionene polymer to be administered will be determined on an individual basis, and will be determined at least in part, by consideration of the individual's size, the severity of symptoms to be treated and the result sought. As used herein, a therapeutically effective amount refers to an appropriate amount of active ingredient (ionene polymer) to obtain therapeutic or prophylactic effect and can be determined by standard pharmaceutical procedures in cell cultures or experimental animals. Typical dosages range from between about 0.05 μg/kg body weight to about 500 mg/kg body weight, more typically between about 0.1 μg/kg body weight to about 100 mg/kg body weight and even more typically even more typically between about 0.5 μg/kg body weight and about 10 mg/kg body weight.

The polymer can be administered alone or in a pharmaceutical composition comprising the polymer, a pharmaceutically acceptable carrier, and optionally, one or more additional drugs. The polymers can be administered, for example, topically, vaginally, orally, intranasally, by aerosol or rectally. The form in which the polymer is administered, for example, powder, tablet, capsule, solution, or emulsion, depends in part on the route by which it is administered. Suitable carriers and diluents will be immediately apparent to persons skilled in the art. These carrier and diluent materials, either inorganic or organic in nature, include, for example, gelatin, albumin, lactose, starch, magnesium stearate preservatives (stabilizers), melting agents, emulsifying agents, salts and buffers. For topical administration, examples of pharmaceutically acceptable carriers include, for example, commercially available inert gels, or liquids supplemented with albumin, methyl cellulose or a collagen matrix. Typical of such formulations are ointments, creams and gels. The therapeutically effective amount can be administered in a series of doses separated by appropriate time intervals such as minutes or hours.

Microbial infections which can be treated by administering a therapeutically effective amount of an ionene polymer or a pharmaceutical composition thereof to a mammal infected with a microbe include, but are not limited to, bacterial infections, such as infection by *Streptococcus, Salmonella, Campylobacter, Helicobacter, Burkholderia, Actinomyces, Eschericha coli, Clostridium* (e.g., *Clostridium difficile*), *Staphylococcus, Shigella, Pseudomonas, Eikenella corrodens, Actinobacillus actinomycetemcomitans, Bacteriodes gingivalis, Capnocytophaga, Wolinella recta, Bacteriodes intermedius, Mycoplasma, Treponema, Peptostreptococcus micros, Bacteriodes forsythus, Fusobacteria, Selenomonas sputigena, Bacteriodes fragilis,* and *Enterobacter cloacae*. Other microbial infections include viral infections, protozoal infections, mycoplasma infections, fungal infections, and parasitic infections.

In one preferred embodiment, polymers and polymer compositions are administered to the oral cavity for treatment of infections of the mouth. In another preferred embodiment, polymers and polymer compositions of the invention are administered orally for treatment of microbial infections in the gastrointestinal tract of a mammal. In yet another preferred embodiment, polymers and polymer compositions of the invention are administered topically for treatment of ocular microbial infections or for treatment of microbial infections on the skin of a mammal. One example of treatment of infections on the skin of a mammal is a wound management regimen that includes a polymer or composition of the invention alone or in combination with a tissue sealant or other wound repair product as is known in the art.

In another preferred embodiment, antimicrobial polymers and polymer compositions of the invention are administered in aerosolized form for treatment of pulmonary infections. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, the entire teachings of which are incorporated herein by reference). Polymer compositions of the invention to be delivered as aerosols for treatment of pulmonary infection are formulated such that an effective dose may be aerosolized (e.g. using a jet or ultrasonic nebulizer) to a particle size optimal for treatment of pulmonary infections. Examples of a suitable particle size for delivery into the endobronchial space is generally about 1 to 5 microns.

The ionene polymers and compositions of the invention are also particularly useful for inhibiting the growth and dissemination, of microorganisms, particularly on surfaces wherein such growth is undesirable. The term "inhibiting the growth of microorganisms" means that the growth, dissemination, accumulation, and/or the attachment, e.g. to a susceptible surface, of one or more microorganisms is impaired, retarded, eliminated or prevented. In a preferred embodiment, the antimicrobial compositions of the inventions are used in methods for inhibiting the growth of an organism on susceptible surfaces in health-related environments. The term "health-related environment" as used herein includes all those environments where activities are carried out directly or indirectly, that are implicated in the restoration or maintenance of human health. A health-related environment can be a medical environment, where activities are carried out to restore human health. An operating room, a doctor's office, a hospital room, and a factory making medical equipment are all examples of health-related environments. Other health-related environments can include industrial or residential sites where activities pertaining to human health are carried out such as activities including food processing, water purification, recreational water maintenance, and sanitation.

The term "susceptible surface" as used herein refers to any surface whether in an industrial or medical setting, that provides an interface between an object and the fluid. A surface, as understood herein further provides a plane whose mechanical structure, without further treatment, is compatible with the adherence of microorganisms. Microbial growth and/or biofilm formation with health implications can involve those surfaces in all health-related environments. Such surfaces include, but are not limited to, scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherally insertable central venous catheters, dialysis catheters, long term tunneled central venous catheters, peripheral venous catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses, (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like.

Other surfaces include the inner and outer surfaces of pieces of medical equipment, medical gear worn or carried by personnel in the health care settings and protective clothing for biohazard or biological warfare applications. Such surfaces can include counter tops and fixtures in areas used for medical procedures or for preparing medical apparatus, tubes and canisters used in respiratory treatments, including the administration of oxygen, solubilized drugs in nebulizers, and anesthetic agents. Additional surfaces include those surfaces intended as biological barriers to infectious organisms such as gloves, aprons and faceshields.

Surfaces in contact with liquids are particularly prone to microbial growth and/or biofilm formation. As an example, those reservoirs and tubes used for delivering humidified oxygen to patients can bear biofilms inhabited by infectious agents. Dental unit waterlines similarly can bear biofilms on their surfaces, providing a reservoir for continuing contamination of the system of flowing and aerosolized water used in dentistry.

Other surfaces related to health include the inner and outer surfaces of equipment used in water purification, water storage and water delivery, and those articles involved in food processing equipment for home use, materials for infant care and toilet bowls.

In accordance with the invention, a method for preventing, inhibiting or eliminating the growth, dissemination and/or accumulation of microorganisms on a susceptible surface (including but not limited to the formation of biofilms) comprises the step of contacting such surface with an antimicrobial agent, or composition thereof of the invention, with an amount sufficient to prevent, inhibit or eliminate such growth, dissemination and/or accumulation, i.e., with an effective amount.

As used herein "contacting" refers to any means for providing the compounds of the invention to a surface to be protected from, microbial growth and/or biofilm formation. Contacting can include spraying, wetting, immersing, dipping, painting, bonding, coating, adhering or otherwise providing a surface with a compound or composition in accordance with the invention. A "coating" refers to any temporary, semipermanent, or permanent layer, covering a surface. A coating can be a gas, vapor, liquid, paste, semisolid or solid. In addition a coating can be applied as a liquid and solidify into a hard coating. Examples of coatings include polishes, surface cleaners, caulks, adhesives, finishes, paints, waxes, polymerizable compositions (including phenolic resins, silicone polymers, chlorinated rubbers, coal tar and epoxy combinations, epoxy resins, polyamide resins vinyl resins, elastomers, acrylate polymers, fluoropolymers, polyesters and polyurethane, latex). Silicone resins, silicone polymers (e.g. RTV polymers) and silicone heat cured rubbers are suitable coatings for use in the invention and described in the art. Coatings can be ablative or dissolvable, so that the dissolution rate of the matrix controls the rate at which the compositions of the invention are delivered to the surface. Coatings can also be non-ablative, and rely on diffusion principals to deliver a composition of the invention to the target surface. Non-ablative coatings can be porous or non-porous. A coating containing an antimicrobial agent of the invention freely dispersed in a polymer binder is referred to as a "monolithic" coating. Elasticity can be engineered into coatings to accommodate pliability, e.g. swelling or shrinkage of the surface to be coated.

Other means for contacting include a sustained or controlled release system that provides constant or prolonged release of an agent of the invention from a susceptible surface. This can be accomplished through the use of diffusional systems, including reservoir devices in which a core of an agent of the invention is surrounded by a porous membrane or layer, and also matrix devices in which the compound is distributed throughout an inert matrix. Materials which may be used to form reservoirs or matrices include silicones, acrylates, methacrylates, vinyl compounds such as polyvinyl chloride, olefins such as polyethylene or polypropylene, fluoropolymers such as polytetrafluoroethylene or polypropylene, fluoropolymers such as polytetrafluorethylene, and polyesters such as terephthalates. Alternatively, the compositions of the invention may be mixed with a resin, e.g., polyvinyl chloride and then molded into a formed article, which integrally incorporates the compound to form a structure having a porous matrix which allows diffusion of the compound or a functional portion thereof into the surrounding environment. Microencapsulation techniques can also be used to maintain a sustained focal release of a compound of the invention.

Other means for providing the antimicrobial agents of the invention to a susceptible surface will be apparent to those of skill in the art.

The compounds and compositions of the invention are also useful for preventing microbial growth and/or biofilms in industries outside of health-related industries, such as industrial systems wherein the presence of an aqueous environment leads to biofilm formation. Examples of such systems include metal working fluids, cooling waters (e.g. intake cooling water, effluent cooling water, recirculating cooling water), and other recirculating water systems such as those used in papermaking or textile manufacture. Marine industries are also plagued by unwanted biofilms such as those that form on boat hulls and other marine structures.

Another embodiment of the present invention is an article comprising a polymer of the present invention in an amount sufficient to prevent, inhibit or eliminate the growth or dissemination of a microorganism or the formation of a biofilm, i.e., an "effective amount." The polymer can be in the article or on the surface of the article. Preferably, the article is coated with a composition comprising an effective amount of a polymer of the present invention. Articles that are advantageously coated with a polymer of the present invention are those in which inhibition of the growth of microorganisms and/or biofilms is desirable, e.g., medical devices, medical furniture and devices exposed to aqueous environments. Examples of such articles are described above.

Ionene polymers of the present invention can be prepared by a reacting a divalent electrophile such as an α,ω-dihalogenated alkane or a corresponding diepoxide with a divalent nucleophile such as 4,4'-trimethylenedipiperidine or N,N,N',N'-tetramethyl-1,3-propanediamine (other examples of divalent nucleophiles are provided in the Examples). When preparing a polyguanidine, the divalent nucleophile is an α,ω-diaminoalkane or an α,ω-aminoguanidine and the divalent electrophile typically is an α,ω-biscyanoguanidine. Polymerizing with one divalent electrophile and one divalent nucleophile results in a homopolymer. Polymerizing with two or more divalent electrophiles and/or divalent nucleophiles results in a copolymer. Such homopolymers and copolymers are encompassed within the present invention.

A preferred method of preparing ionene polymers of the present invention comprises the step of reacting a diamine (e.g., an α,ω-diaminoalkane, an α,ω-alkylenedipyridine, or an α,ω-alkylenedipiperidine, a diepoxide (e.g., a straight chained alkane where the epoxide groups are at the termini of the molecule), and an acid. Preferably, each amine of the diamine is tertiary and/or the diamine comprises two heterocycles. Preferred heterocycles can be either aromatic or non-aromatic, as represented by the structural formulas:

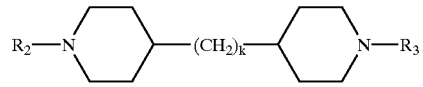

and

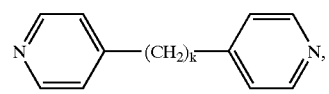

where k is an integer from 1 to 10, and $R_2$ and $R_3$ are as defined above. Preferred diepoxides are represented by the structural formula:

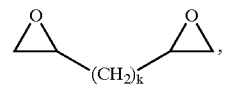

where k is as defined above. Suitable acids for this method include acetic acid, carbonic acid, phenol, substituted phenols, benzoic acid, ascorbic acid, formic acid, salicylic acid, propionic acid, citric acid, adipic acid, oxalic acid, amino acids, lactic acid, glycolic acid, boric acid, malonic acid, caproic acid, hydrochloric acid, triflic acid, toluenesulfonic acid, methylsulfonic acid, benzenesulfonic acid, succinic acid, and boronic acids.

Polyionene polymers are typically "capped" at the termini with a partially reacted divalent electrophile or nucleophile or a monovalent electrophile or nucleophile. For example, when polymerizing 4,4'-trimethylenepyridine and 1,6-dibromohexane (or the corresponding epoxide), the resulting polymer is capped at either end with one of the following groups:

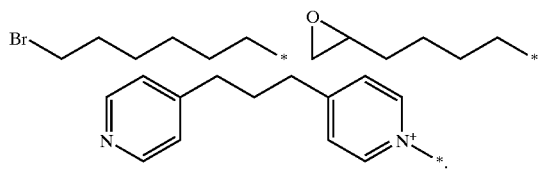

Optionally, the capping group can be reacted further, for example, by hydrolyzing the epoxide or reacting the halide or epoxide with a nucleophile. An example of a capping group for polyguanidine polymers or copolymers is represented by Structural Formula (XXXIV):

(XXXIV)

where $R_{11}$ is a C2–C90 alkyl, C2–C90 oxyalkyl, or aromatic group and the symbol "*" represents the bond connecting the cap to the polymer or copolymer.

Ionene polymers of the invention may also be cross-linked with primary, secondary or other polyfunctional amines using means known in the art. Ionene polymers can be cross-linked by polymerizing in the presence of a multivalent nucleophile (i.e., a compound with three or more nucleophilic groups such as a triamine or tetraamine) or a multivalent electrophile (i.e., a compound with three or more nucleophilic groups such as a trihalide or tetrahalide).

The invention will now be further and specifically described by the following non-limiting Examples.

EXAMPLES

Preparation of Poly(hexamethylene biguanidine-alt-4,9-dioxadodecylbiguanide) (XVIII)

Hexamethylenebiscyanoguanidine (3.99 mmoles, 1.00 g) and 4,9-dioxa-1,12-dodecanediamine (3.99 mmoles, 0.848 ml) were added to a 40 mL vial with a septa-cap followed by 2 equivalents of concentrated HCl. The mixture was heated to 135–145° C. in a shaker overnight. The resulting clear yellow, brittle solid was dissolved in water and purified by centrifugation through a 3K Macrosep filtration membrane.

Preparation of Poly(4,4'-trimethylenebis(1-methylpiperidinium)-alt-1,8-octane) (II)

4,4'-Trimethylenebis(1-methylpiperidine)-alt-1,8-Dibromooctane was prepared by dissolving 4,4'-Trimethylenebis(1-methylpiperidine)(39.9 mL) in 30 ml of DMF in a 250 mL Erlenmeyer flask. 1,8 Dibromooctane (27.63 mL) was also added to the flask. The reaction was purged with nitrogen, covered with a septum, and stirred with a magnetic stir plate. The initial solution was clear. After approximately 20 minutes of stirring the reaction exothermed and solidified. A light yellow solid polymer formed and was left to further polymerize for a week. The polymer was dissolved in ~300 mL of deionized water and dialyzed (3500 molecular weight cut-off) in water 3× and 1× in water/MeOH 70%/30%.

Preparation of Poly(4-(dimethylamino)phenyldiphenylphosphine-alt-dodecane) (IX)

4-(Dimethylamino)phenyldiphenylphosphine (1.73 mmoles, 0.529 g) and 1,12-dibromododecane (1.73 mmoles, 0.569 g) were dissolved in DMF (1 mL) and shaken for 1 week. The resulting viscous liquid was diluted with water and purified by centrifugation through a 3K Macrosep.

Preparation of Poly(4,4'-trimethylenedipyridinium-alt-hexane) (XIX)

4,4'-Trimethylenedipyridine (3.46 mmoles, 0.687 g) was added to a 40 ml vial followed by 2.3 ml of DMF/methanol (1:1 v:v). 1,6-dibromohexane (3.46 mmoles, 0.533 ml) was added and the vial was capped with a septa-cap. The vial was purged with nitrogen and placed in a shaker for 1 week. The resulting clear orange viscous solution was diluted in water and purified by centrifugation through a 3K Macrosep.

Preparation of Poly(4,4'-trimethylenedipyridinium-alt-nonane) (XX)

4,4'-Trimethylenedipyridine (3.46 mmoles, 0.687 g) was added to a 40 ml vial followed by 2.3 ml of DMF/methanol (1:1 v:v). 1,9-dibromononane (3.46 mmoles, 0.705 ml) was added and the vial was capped with a septa-cap. The vial was purged with nitrogen and placed in a shaker for 1 week. The resulting light orange waxy solid was dissolved in water and purified by centrifugation through a 3K Macrosep.

Preparation of Poly(N,N-dimethylpropylammonium-alt-N,N-dimethylhexylammonium) (VIIIb)

N,N,N',N'-Tetramethyl-1,3-propanediamine (31.9 ml) was dissolved in 40 ml of DMF in a 250 Erlenmeyer flask. 1,6-Dibromohexane (29.3 ml) was added to the flask. The reaction was purged with nitrogen, covered with a septum, and stirred with a magnetic stir plate. The initial solution was clear. A very quick reaction that exothermed and solidified occurred. An off white solid polymer formed and was left to further polymerize for a week. The polymer was dissolved in approximately 300 ml of deionized water and dialyzed (3500 MW) in water 3× and 1× in water/MeOH 70%/30%.

Preparation of Poly(hexamethylenebisguanide-alt-nonanebiguanide) (XXI)

Hexamethylenebiscyanoguanidine (3.99 mmoles, 1.00 g) and 1,9-diaminononane (3.99 mmoles, 0.623 g) were added to a 40 vial with a septa-cap followed by 2 equivalents of concentrated HCl. The mixture was heated to 135–145° C. in a shaker overnight. The solid was dissolved in water and purified by centrifugation through a 3K Macrosep filtration membrane.

Preparation of Poly(4,4'-trimethylenedipiperidinium-alt-hexane) (III)

4,4'-Trimethylenedipiperidine (3.466 mmoles, 1.139 g) was added to a 40 ml vial followed by 2 ml DMF/MeOH (1:1v). 1,6-Dibromohexane (3.466 mmoles, 0.533 ml) was added and the vial was capped with a septa-cap. The vial was purged with nitrogen and placed in a shaker for 1 week. The resulting opalescent waxy solid was dissolved in water and purified by centrifugation through a 3K Macrosep.

Preparation of Poly(hexamethylene-biscyanoguanidine-alt-hydrazine) (XIII)

Hexamethylene-biscyanoguanidine (4.00 mmoles, 1.00 g) and hydrazine (4.00 mmoles, 0.274 g) were added to a 40 ml vial with a septa-cap followed by 2 equivalents of concentrated HCl. The mixture was heated to 165° C. in an oil-bath for 3 h. The resulting pink foam was acidified with 2 equivalents concentrated HCl, dissolved in water and purified by centrifugation through a 3K Macrosep filtration membrane.

Preparation of Poly(4-(dimethylamino)phenyldiphenylphosphine-alt-nonane) (IX, where R7 is nonyl)

4-(Dimethylamino)phenyldiphenylphosphine (1.73 mmoles, 0.529 g) and 1,9-dibromononane (1.73 mmoles, 0.352 g) were dissolved in DMF (1 ml) and shaken for 1 week. The resulting viscous liquid was diluted with water and purified by centrifugation through a 3K Macrosep.

Preparation of Poly(4-(dimethylamino)phenyldiphenylphosphine-alt-decane) (IX, where R7 is decyl)

4-(Dimethylamino)phenyldiphenylphosphine (1.73 mmoles, 0.529 g) and 1,10-dibromodecane (1.73 mmoles, 1.04 g) were dissolved in DMF (1 ml) and shaken for 1 week. The resulting viscous liquid was diluted with water and purified by centrifugation through a 3K Macrosep.

Preparation of Poly (hexamethylenebiscyanoguanidine-alt-1,3-aminoguanidine) (XIV)

Hexamethylene biscyano guanidine (4.00 mmoles, 1.00 g) and 1,3-aminoguanidine (4.00 mmoles, 0.502 g) were added to a 40 ml vial with a septa-cap followed by 2 equivalents of concentrated HCl. The mixture was heated to 165° C. in an oil-bath for 3 h. The resulting orange solid was acidified with 1 eq. concentrated HCl, dissolved in water and purified by centrifugation through a 3K Macrosep filtration membrane.

Preparation of Poly(1,3-bis(diphenylphosphonium) propane-alt-butane) (X)

1,3-Bis(diphenylphosphino)propane (1.33 mmoles, 0.550 g) and 1,4-dibromobutane (1.33 mmoles, 0.159 g) were dissolved in DMF (0.769 ml) and shaken for 1 week. The resulting viscous liquid was diluted with water and purified by centrifugation through a 3K Macrosep.

Preparation of Poly(4-(dimethylamino) phenyldiphenylphosphine-alt-butane) (IX, where R7 is butyl)

4-(Dimethylamino)phenyldiphenylphosphine (1.73 mmoles, 0.529 g) and 1,4-dibromobutane (1.73 mmoles, 0.207 g) were dissolved in DMF (1 ml) and shaken for 1 week. The resulting viscous liquid was diluted with water and purified by centrifugation through a 3K Macrosep.

Preparation of Poly(1,4-bis(diphenylphosphonium) butane-alt-butane) (XI)

1,4-Bis(diphenylphosphino)butane (2.31 mmoles, 0.986 g) and 1,4-dibromobutane (2.31 mmoles, 0.276 g) were dissolved in DMF (1.333 ml) and shaken for 1 week. The resulting viscous liquid was diluted with water and purified by centrifugation through a 3K Macrosep.

Preparation of Crosslinked Polymers—Post-polymerization Crosslinking

Hydroxyl-containing polymer (XVI) was cross-linked with 6 mole % 1,6-diisocyanatohexane in DMF to produce a gel. The gel was washed with 70% methanol-water and lyophilized.

Preparation of Crosslinked Polymers—In situ Crosslinking

N,N,N',N'-Tetramethyl-1,3-propanediamine (34.64 mmoles, 5.795 ml), 1,9-dibromononane (34.64 mmoles, 7.048 ml), and 1,3,5-tris(bromomethyl)-2,4,6-trimethylbenzene (3.464 mmoles, 1.383 g) were dissolved in DMF (1 ml) and shaken for a week at room temperature. The resulting white gel was washed with hot DMF, methanol, and water and lyophilized.

Preparation of poly(trimethylenedipyridinium-alt-2, 7-dihydroxyoctane) (XVI)

Trimethylenedipyridine (100 g) was placed in a roundbottom flask. To the flask was added 1,2,7,8-diepoxyoctane (71.72 g). The reaction was stirred under nitrogen at room temperature for 20 min. until nearly all the trimethylene-dipyridine was dissolved. At this time, acetic acid (121 g) was slowly added dropwise over a 24 hr period. The reaction was stirred at room temperature for an additional four days. The resulting material was dark blue and highly viscous. The solid was dissolved in water and purified by tangential flow with a 1K MWCO membrane.

MIC Assay:

The minimum inhibitory concentration (MIC) assay determines the minimum concentration of an antimicrobial agent required to inhibit growth of the test organisms. MIC assays were performed against a standard panel of organisms as a screening tool to identify compounds that have antimicrobial activity. The MIC assay was subsequently repeated against other specialized microbial panels. Compounds were tested for bacteriocidal activity, for time course of killing, for toxicity against tissue culture cells grown in vitro, and in some cases, for antimicrobial activity in vivo.

The MIC assay was performed according to the *Performance Standards for Antimicrobial Susceptibility Testing,* 1998, vol. M100-S8, Eighth Informational Supplement, NCCLS, 940 West Valley Road, Suite 1400, Wayne, Pa. 19087.

Briefly, polymers to be tested were dissolved in 0.85% saline to a final concentration of either 830 or 1000 µg/ml, the pH was adjusted to 7.0 and the solution was filter-sterilized through a 0.22 µm filter. Two-fold serial dilutions of polymer were prepared in Mueller-Hinton broth with cations aliquotted into 96-well microtiter plates.

The plates were then inoculated with $5 \times 10^5$ cells/ml of target organism, and were incubated 18–24 hr at 35° C. The optical density (OD) was then read at 590 nm, and microorganism growth was scored (OD$\geq$0.1 is considered to be growth; OD<0.1 is considered growth inhibition). The MIC value is defined as the lowest concentration of compound which inhibits growth.

For the antimicrobial polymers of the present invention, these values are <5 µg/ml (see Table 1).

MBC Assay

The minimum bacteriocidal concentration (MBC) of a compound is defined as that concentration which reduces bacterial numbers by $\geq$3 log units after incubation for 18–24 hr. This assay is important to distinguish between compounds which inhibit organisms metabolically and those compounds which kill. The procedure is taken from *Antibiotics in Laboratory Medicine,* V. Lorian, Ed., Williams & Wilkins, Baltimore, 1996.

Briefly, an MIC assay was run and read as described above for the MIC assay. After reading and scoring the MIC plates, 10-fold serial dilutions were prepared from the contents of microtiter test wells containing polymer at concentrations corresponding to 2× the MIC, the MIC, and 0.5× the MIC. Aliquots of these were then plated onto Tryptic Soy Agar plates and were incubated overnight at 37° C. Colonies were then enumerated, and the lowest concentration that reduced colony numbers by $\geq$3 log units was designated the MBC value.

For the antimicrobial polymers of the invention, these values were the same as the MIC value for a given polymer (see Table 1).

TABLE 1

Polymer MIC(ug/ml)

| Formula # | S. aureus (ATCC 29213) | MRSA (5 strains) (1) | GISA (5 strains) (2) | E. faecalis (ATCC 29212) | VRE (4 strains) | P. aeruginosa (ATCC 27853) | Candida* | B. cepacia | Oral pathogens ** | C. difficile | H. pylori (Win) | E. coli (ATCC 25922) | S. marcescens |
|---|---|---|---|---|---|---|---|---|---|---|---|---|---|
| VIII | 0.65 | 1–2 | 1 | 1 | 1–3 | 10.4 | 0.65–1.3 | 41.5 | | 0.65 | 0.2 | 1.3 | 3 |
| II | 0.31 | 1.9 | ≦0.125 | 0.31 | 0.3 | 1.3 | 1.3–2.6 | 5.2 | nd | <0.16 | 0.2 | .65 | 3 |
| IV | 0.65 | 2.2–3.8 | nd | 0.65 | 2–2.6 | 2.6 | 0.32–2.6 | 5.2 | nd | nd | 3 | 1.3 | 9 |
| II | 1.8 | 1–2.6 | nd | 1 | 1–2 | 9 | 3–28 | 28 | nd | nd | 1 | 1 | 3 |
| III | 1.4 | 0.4–1.8 | nd | 3 | 1–3 | 9 | 1–3 | 28 | nd | nd | 2 | 3 | 3 |
| XII | 0.31 | 0.3–0.5 | nd | 0.3 | 0.3 | 0.31 | 0.16–2.6 | 41.5 | nd | nd | nd | 2.6 | 3 |
| XIX | 0.65 | 1 | 0.5 | 1 | 1–3 | 0.65 | 1.3–2.6 | 41.5 | <10 | nd | 1 | 2.6 | 3 |
| XX | 1.3 | 2.2–3 | 16 | 1 | 1–3 | 1.3 | 2.6 | 5.2 | <10 | <0.16 | 0.4 | 1.3 | 3 |
| XXIII | 1 | 1.4–2.2 | nd | 1 | 1–3 | 9 | 3 | 9 | nd | nd | 1 | 3 | 3 |
| IX+ | 1 | nd | nd | 0.3 | nd | 83 | 1–9 | 28 | nd | nd | nd | 3 | 28 |
| IX++ | 1 | 1 | nd | 3 | 3–20 | 83 | 1–9 | 9 | nd | nd | 0.7 | 3 | 9 |
| IX+++ | 0.65 | nd | 8 | 1.25 | nd | 5.2 | 0.65–1.3 | 5.2 | <10 | 2.5 | 1.3 | 2.6 | 3 |

*3 strains *C. glabrata*, 6 strains *C. albicans*, 2 strains *C. tropicalis*, 2 strains *C. Krusei*; ** including: *Actinobacillus actinomycetemcomitans*, *Porphyromonas gingivalis*, *Prevotella intermedia*, *Campylobacter rectus*, *Treponema denticola*, *Streptococcus intermedius*, *Fusobacterium nucleatum*, *Streptococcus gordonii*, and *Actinomyces viscosus*; methacillin resistant *Staphylococcus aureus*; glycopeptide intermediate *Staphylococcus aureus*; + (where R7 is butyl) ++ (where R7 is decyl) +++ (where R7 is dodecyl)

Time Course of Antimicrobial Killing:

The purpose of this assay is to determine how rapidly biocidal compounds of the invention kill microorganisms.

One ml of Mueller Hinton broth with cations was inoculated with $1 \times 10^7$ organisms. An amount of polymer equal to 4× the MIC was added at time point zero ($T_0$), and the mixture was incubated at 37° C. At selected time points (starting at $T_0$) samples were removed, serial ten-fold dilutions were prepared, aliquots were plated on Tryptic Soy Agar plates and were incubated overnight at 37° C. Colonies were then enumerated.

For the antimicrobial polymers studied, killing occurs within 10 min at 4× the MIC.

In vitro Toxicity:

Polymers with high antimicrobial activity were tested for in vitro toxicity against tissue culture cells. Cells were exposed to polymer for 18–24 hr, then were tested for metabolic activity using the mitochondrial redox indicator dye AlomarBlue® (AccuMed International, Inc., Chicago, Ill.) following the manufacturer's instructions.

Three different cell lines were used: AGS cells (an immortalized gastric cell line), CHO (Chinese Hamster Ovary) cells, and MDBK (Madin Darby Bovine Kidney) cells. Cells were plated into 96-well microtiter plates in RPMI or MEM culture medium containing 10% fetal bovine serum (FBS) at $1-5 \times 10^4$ cells/well, and were grown 1–2 days 37° C. until confluent. Serial 2-fold dilutions of test polymer were prepared in MEM with 10% FBS. The medium was aspirated from confluent tissue culture cells, was replaced with 100 µl of polymer solution, and plates were incubated overnight at 37° C. The next day, cells were washed 2× with MEM (without phenol red or FBS), were overlaid with MEM lacking phenol red or FBS but containing AlomarBlue®, were incubated 4 hr at 37° C., and plates were read in a fluorimeter using 530 nm excitation and 590 nm for reading fluorescence. Values are expressed as percent of untreated controls, and the $ED_{50}$ was determined by regression analysis.

For the antimicrobial polymers of the invention, the $ED_{50}$ was between 50–100× the MIC (data not shown).

In vivo Toxicity:

In vivo toxicity of the polymer of Formula II was assayed in mice. Groups of 5 animals were dosed twice daily for 5 days by oral gavage at a dose of 10, 100, or 500 mg/kg body weight. Animals were assessed daily, and deaths were recorded. The dose at which ½ the animals died was considered the $LD_{50}$. The $LD_{50}$ was >100 mg/kg (Data not shown).

In vivo Studies: Proliferation of *S. aureus* in Wounds:

Studies have been done examining clearance of *S. aureus* from partial thickness dermal wounds in pigs [Mertz, P. M., O. M. Alvarez, R. V. Smerbeck, and W. H. Eaglstein. 1984. A new in vivo model for the evaluation of topical antiseptics on superficial wounds. The effect of 70% alcohol and povidone-iodine solution. *Arch Dermatol.* 120:58–62.]. The pig model was chosen because pig skin is most similar to human. Groups of 6 partial thickness wounds were made on the backs of 25–30 kg specific pathogen-free pigs. Wounds were inoculated with $5 \times 10^4$ colony forming units (CFU) of *S. aureus* (ATCC #6538), then were either treated with approximately 100 µl of a solution containing 10 mg/ml of the polymer of Formula II or were left as untreated controls. On each of 3 successive days, a pair of wounds was processed in duplicate for quantitative recovery of *S. aureus*, and the remaining wounds were again treated with 100 µl of the polymer of Formula II. Recovered colonies of *S. aureus* were enumerated, and compared with untreated controls.

Treatment with the polymer of Formula II resulted in 5-log reduction in recovered CFU compared with untreated controls (data not shown). In this model, a reduction of 1-log is considered significant.

In vivo Studies: Wound Healing

Studies have been done examining the effect of the polymer of Formula II on healing of partial thickness excisional wounds in pigs, following the protocol of Eaglstein and Mertz [Eaglstein, W. H., and P. M. Mertz. 1978. "New methods for assessing epidermal wound healing: the effects of triamcinolone acetonide and polyethelene film occlusion". *J Invest Dermatol.* 71:382–4.]. Briefly, excisional wounds were made on the back of pigs on Day 0; wounds were then treated daily (starting on Day 0) for the next 5 days. Healing is monitored by assessing epithelization both histopathologically and by measuring the ability of dermis to separate from the epidermis in excised wound biopsies following treatment for 24 hr at 37° C. with 0.5 M NaBr.

By Day 6, 50% of wounds treated with the polymer of Formula II were epithelized, compared with 20% of controls. All wounds were epithelized by Day 8. This suggests that the polymer of Formula II does not impede wound healing, and appears to accelerate healing.

Antimicrobial Polymers Against *Helicobacter pylori* In Vivo:

*Helicobacter pylori* infection is associated with development of peptic ulcer disease and gastric cancer. Antimicrobial polyionenes have been tested in vivo against *H. pylori*. In the 'acute' model, C57BL/6 mice were orally inoculated with $10^6$–$10^7$ colony forming units (CFU) of the mouse-adapted Sydney strain of *H. pylori* ~3 months before initiating the study. On the day of the study, groups of 4–7 animals were anesthetized and surgery was performed to ligate the pylorus of the stomach. 0.1 ml of a 20 mg/ml solution of Formula II in phosphate-buffered saline (PBS), or PBS alone in the control groups, was introduced into the stomach by oral gavage. After 4 hours, animals were sacrificed, the fundus and antrum homogenized in PBS and serial dilutions of the homogenate plated on *Helicobacter*-selective plates (Brucella agar with 5% sheep's blood, 10 mg/ml vancomycin, 0.33 mg/L polymyxin B, 20 mg/L bacitracin, 1.07 mg/L nalidixic acid and 5 mg/ml amphotericin B). Plates were incubated 5 days at 37° C. under microaerophilic conditions. Colonies were then enumerated and animals treated with the polymer of Formula II compared with controls that had received PBS only. Groups that received polyionene showed 67–76% reduction in *H. pylori* CFU compared with controls.

These in vivo findings were extended in a second "chronic" mouse study in which polymer was administered by gavage for a 4 day period at a dose of 50 mg/kg/day, twice a day. Twenty-four hours after the last polymer administration the mice were sacrificed and the number of viable *H. pylori* in the gastric mucosa was determined as in the acute study. Groups that received the polyionene polymer of Formula II showed 39–48% reduction in *H. pylori* CFU compared with controls. This suggests that the polymer of Formula II confers some protection against disease.

In a 5-day oral toxicity study in mice the polymer of Formula II was well tolerated at a dose of 10 mg/kg/day administered b.i.d. At 100 mg/kg/day moderate toxicity was evident.

Antimicrobial Polyionenes Against *Clostridium difficile* in Hamsters:

*Clostridium difficile*-induced colitis is a frequent consequence of therapy using broad-spectrum antibiotics. A preliminary study was done to assess polyionene treatment of *C. difficile* disease in the hamster model. Groups of 10 Syrian Golden hamsters (BioBreeders, Inc) were inoculated by oral gavage with $10^5$ CFU of HUC 2-4 strain (A. Onderdonk, Harvard Medical School) of *C. difficile* on Day-1. Animals received 10 mg/kg Cleocin Phosphate® on Day 0. On Day 1 through Day 6 animals received 3 doses/day (0.75 ml/dose saline (controls) or the polymer of Formula II by oral gavage totaling 10 mg/animal/day. Animals were scored for survival on Day 6. Forty percent of animals receiving the ionene polymer of Formula II survived through Day 6, whereas only 10% of controls did so, indicating that the polymer of Formula II conferred a level of protective effect against *C. difficile* disease.

Polyionene Polymers Are Effective in Treating Mucositis in a Hamster Model Following Radiation Therapy:

Oral mucositis is a frequent sequel to chemotherapeutic treatment for a number of cancers, as well as of irradiation for head and neck tumors. While the precise causes of mucositis remain unknown, oral microflora are thought to be involved in both the induction and exacerbation of disease. The efficacy of polyionene polymers in treating oral mucositis was assayed according to a hamster model disclosed in Sonis et al., *Oral Oncology* 36:373 (2000), the entire teachings of which are incorporated herein by reference. Briefly, male Golden Syrian hamsters (Charles River Laboratories), aged 5 to 6 weeks, with body weights of approximately 90 g at project commencement, were used. Mucositis was induced using an acute radiation protocol. A single dose of radiation (35–40 Gy/dose) was administered to all animals on Day 0. Radiation was generated with a 250 kilovolt potential (15 mA) source at a focal distance of 50 cm, hardened with a 0.35 mm Cu filtration system. Irradiation targeted the left buccal pouch mucosa at a rate of 121.5 cGy/minute. Prior to irradiation, animals were anesthetized with an intraperitoneal injection of sodium pentobarbital (80 mg/kg). The left buccal pouch was everted, fixed and isolated using a lead shield.

All animals were dosed with test material three times per day. A needleless tuberculin syringe containing 0.5 ml of the test compound was inserted into the left cheek pouch and the drug deposited into the pouch. Dosing began on Day 0 and continued until Day 19.

For the evaluation of mucositis, the animals were anesthetized with inhalation anesthetics, and the left pouch everted. Mucositis was scored visually by comparison to a validated photographic scale, ranging from 0 for normal to 5 for severe ulceration. In descriptive terms, this scale is defined as follows:

| Score | Description |
| --- | --- |
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray appearance due to a pseudomembrane. Cumulative size of ulcers should equal about ¼ of the pouch. Severe erythema and vasodilation. |
| 4 | Cumulative size of ulcers should equal about ½ of the pouch. Loss of pliability. Severe erythema and vasodilation. |
| 5 | Virtually all of pouch is ulcerated. Loss of pliability (pouch can only partially be extracted from mouth). |

A photograph was taken of each animal's cheek pouch mucosa using a standardized technique. At the conclusion of the experiment, all films were developed and the photographs randomly numbered. At least two independent trained-observers graded the photographs in blinded fashion using the above-described scale (blinded scoring). A score of 1–2 is considered to represent a mild stage of the disease, whereas a score of 3–5 is considered to indicate moderate to severe mucositis in which frank ulceration of the cheek pouch is evident. Treatment efficacy was measured by the reduction in time that the animals experienced ulcerative mucositis (a score <3) expressed as a percentage of the time that the animals in the control group experienced ulcerative mucositis (a score >3). Animals treated with polyionene compounds experienced a significant reduction in the percent time they experienced ulcerative mucositis. For example, animals treated with II at 1 mg/ml had a 46% reduction in ulcerative mucositis when compared to the control group.

Those skilled in the art will recognize or be able to ascertain using no more than routine experimentation many equivalents to the specific embodiments of the invention described herein. Such equivalents are intended to be encompassed in the scope of the following claims.

What is claimed is:

1. A polymer or copolymer characterized by a repeat unit having the formula:

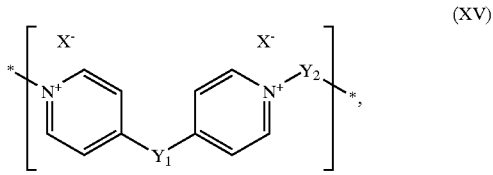

(XV)

wherein $Y_1$ and $Y_2$ are independently a lower alkylene or lower alkylene glycol group, provided that $Y_2$ is substituted with two or more alcohol groups; each $X^-$; separately or taken together, is a physiologically acceptable anion; and said polymer or copolymer is substantially free of diphenol.

2. The polymer of claim 1, wherein said polymer is a homopolymer.

3. The polymer or copolymer of claim 1 wherein the polymer or copolymer is characterized by repeat units of formula XVI or XVII:

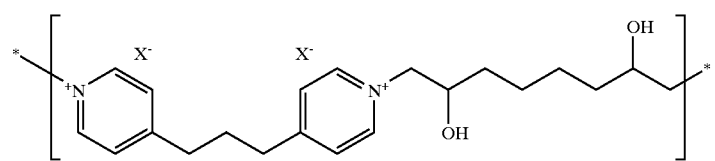

(XVI)

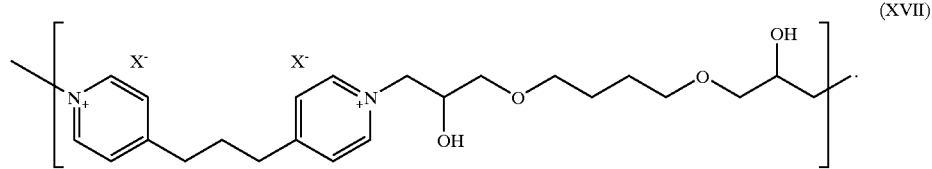

(XVII)

4. A pharmaceutical composition comprising a physiologically acceptable carrier or diluent and a polymer or copolymer characterized by a repeat unit having the formula:

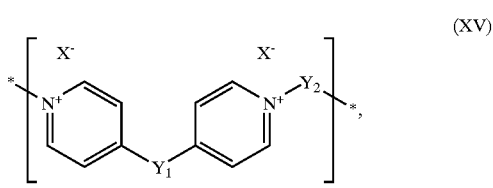

(XV)

wherein $Y_1$ and $Y_2$ are each independently a substituted or unsubstituted lower alkylene or lower alkylene glycol group; and each $X^-$, separately or taken together, is a physiologically acceptable anion.

5. The pharmaceutical composition of claim 4, wherein at least one lower alkylene or lower alkylene glycol group represented by $Y_1$ and $Y_2$ is substituted.

6. The pharmaceutical composition of claim 4, wherein the polymer or copolymer is characterized by repeat units of formula XVI or XVII:

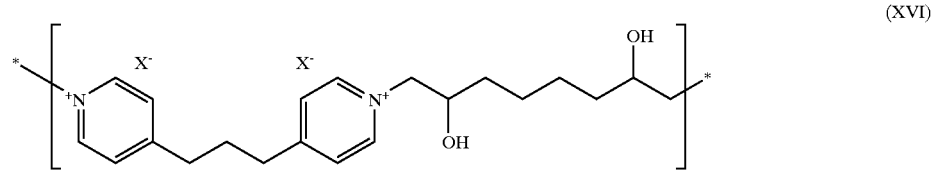

(XVI)

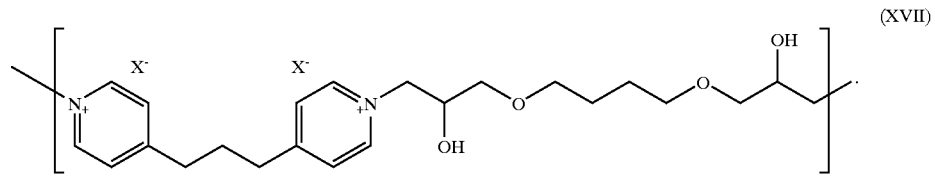

(XVII)

7. A method of treating a microbial infection in a mammal comprising the step of administering to said mammal a therapeutically effective amount of a polymer or copolymer of claim 1.

8. A method of treating a microbial infection in a mammal comprising the step of administering to said mammal a therapeutically effective amount of a homopolymer of claim 2.

9. A method of treating a microbial infection in a mammal comprising the step of administering to said mammal a therapeutically effective amount of a polymer or copolymer of claim 3.

10. A method of treating a microbial infection in a mammal comprising the step of administering to said mammal a therapeutically effective amount of a pharmaceutical composition of claim 4.

11. A method of treating a microbial infection in a mammal comprising the step of administering to said mammal a therapeutically effective amount of a pharmaceutical composition of claim 5.

12. A method of treating a microbial infection in a mammal comprising the step of administering to said mammal a therapeutically effective amount of a pharmaceutical composition of claim 6.

13. A method of inhibiting the growth of a microorganism on a surface comprising the step of contacting said surface with an effective amount of a polymer or copolymer of claim 1.

14. A method of inhibiting the growth of a microorganism on a surface comprising the step of contacting said surface with an effective amount of a homopolymer of claim 2.

15. A method of inhibiting the growth of a microorganism on a surface comprising the step of contacting said surface with an effective amount of a polymer or copolymer of claim 3.

16. A pharmaceutical composition comprising a polymer or copolymer characterized by a repeat unit having the formula:

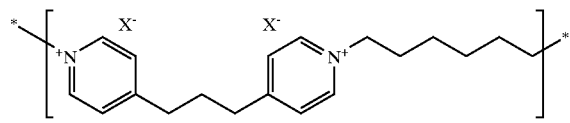

(XIX)

and a pharmaceutically acceptable carrier or diluent, wherein each X⁻, separately or taken together, is a pharmaceutically acceptable anion.

17. A method of treating a microbial infection in the gastrointestinal tract of a mammal comprising the step of administering to said mammal a therapeutically effective amount of a pharmaceutical composition of claim 16.

18. A pharmaceutical composition comprising a polymer or copolymer characterized by a repeat unit having the formula:

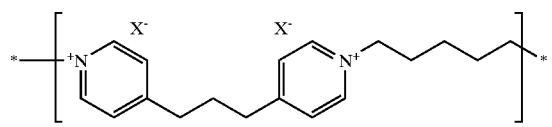

(XXII)

and a pharmaceutically acceptable carrier or diluent, wherein each X⁻, separately or taken together, is a physiologically acceptable anion.

19. A method of treating a microbial infection of the oral mucosa or gastrointestinal tract of a mammal comprising the step of administering to said mammal a therapeutically effective amount of a pharmaceutical composition of claim 18.

20. A copolymer characterized by a repeat unit having the formula:

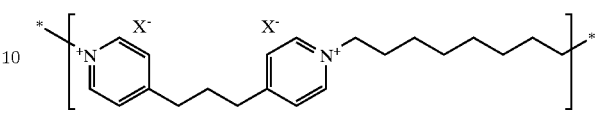

(XXIII)

wherein each X⁻, separately or taken together, is a physiologically acceptable anion.

21. A pharmaceutical composition comprising a polymer or copolymer characterized by a repeat unit having the formula:

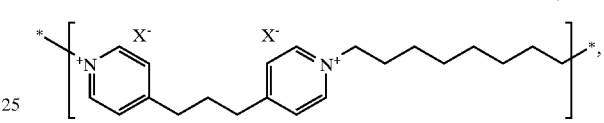

(XXIII)

and a pharmaceutically acceptable carrier or diluent, wherein each X⁻, separately or taken together, is a physiologically acceptable anion.

22. A method of treating a microbial infection in a mammal comprising the step of administering to said mammal a therapeutically effective amount of a copolymer of claim 20.

23. A method of treating a microbial infection in a mammal comprising the step of administering to said mammal a therapeutically effective amount of a pharmaceutical composition of claim 21.

24. A method of inhibiting the growth of a microorganism on a surface comprising the step of contacting said surface with an effective amount of a copolymer of claim 20.

25. A pharmaceutical composition comprising a physiologically acceptable carrier or diluent and a polymer or copolymer characterized by a repeat unit having the formula:

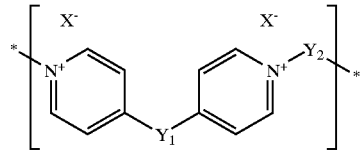

(XV)

wherein $Y_1$ and $Y_2$ are each independently a lower alkylene or lower alkylene glycol group, provided that $Y_2$ is substituted with two or more alcohol groups; and each X⁻, separately or taken together, is a physiologically acceptable anion.

26. A method of treating a microbial infection in a mammal comprising the step of administering to said mammal a therapeutically effective amount of a pharmaceutical composition of claim 25.

* * * * *